United States Patent [19]

Louderback et al.

[11] 3,943,364

[45] Mar. 9, 1976

[54] DETERMINING HOMOGENEITY OF CLINICAL CONTROLS

[75] Inventors: Allan L. Louderback, Temple City; Anthony J. Fontana, Glendora, both of Calif.

[73] Assignee: Baxter Laboratories, Inc., Deerfield, Ill.

[22] Filed: Aug. 14, 1974

[21] Appl. No.: 497,420

[52] U.S. Cl. .............................................. 250/303
[51] Int. Cl.$^2$ ....................................... G01T 1/161
[58] Field of Search ................... 250/302, 303, 328; 23/230 B; 252/301.1 R, 408; 424/1

[56] References Cited
OTHER PUBLICATIONS

"Using Tracers in Refinery Control," by D. E. Hull, Nucleonics, Vol. 13, No. 4, Apr. 1955, pp. 18–21.

*Primary Examiner*—Davis L. Willis
*Attorney, Agent, or Firm*—Lawrence W. Flynn; Louis Altman

[57] ABSTRACT

Homogeneity of bulk control serum is determined when making production fills of clinical chemistry control serum using a radioactive tracer in the bulk control serum tank. A radioactive tracer is added to the control serum along with any other added constituents. After standard bottles are filled, they are analyzed for radioactivity in a radiation counter for measuring the amount of radioactive tracer in each bottle and thereby determining the homogeneity of the contents of the bottles.

3 Claims, No Drawings

DETERMINING HOMOGENEITY OF CLINICAL CONTROLS

BACKGROUND OF THE INVENTION

This invention relates to a method of determining homogeneity of the contents of a number of bottles filled on a production line of control materials used in clinical chemistry.

Control materials which simulate analytical samples are essential for the accurate and reliable performance of many clinical tests. These control materials are usually complex mixtures and are commonly derived, in part, from natural sources. They are desirably prepared as a collection of identical samples and are expected to be stable over a designated period of time.

Clinical chemistry control materials are designed for use in analytical systems and in quality control programs to provide means for estimating precision and detecting deviations which result from reagent or instrumentation defects. These control materials also are useful for proficiency testing and interlaboratory surveys. If constituent levels are established with sufficient accuracy and precision, they may also be used as calibration standards.

Illustrative of such clinical chemistry control materials are those described in U.S. Pat. Nos. 3,466,249; 3,558,522; 3,629,142; 3,682,835; 3,705,110; 3,728,226; 3,729,427; and 3,753,925.

Recognizing the need for effective control materials used in the performance of clinical laboratory testing, the National Committee for Clinical Laboratory Standards has recently proposed that certain standards be set up for control materials sold in the United States; *Clinical Chemistry*, Vol. 18 , pp. 585–8 ( 1972 ). Among the criteria established by the NCCLS is that in the preparation of batches of controls, the manufacturer must ensure that there is a sufficient degree of vial-to-vial uniformity in the product so that the user may achieve reproducible results. One prerequisite of this uniformity is the homogeneity of the material being delivered into individual containers. The importance of homogeneity is readily apparent when it is considered that a control serum may contain from a few up to 30 different constituents. These constituents normally are admixed in a large container such as 1000 or 2000 liter kettle and then dispensed into unit vials of various sizes. According to the standards proposed by the National Committee for Clinical Laboratory Standards, inter-vial differences in concentration in the final product due to combined errors of homogeneity and dispensing shall not exceed ± 1.0 percent of the mean value in more than 5 percent of the vials. This represents a coefficient of variation (assuming a normal distribution) of 0.5 percent.

It is difficult to measure homogeneity in a batch of control liquid because the best biochemical test heretofore available is the assay system for sodium. Sodium has a coefficient of variation of about 1½ to 2 percent in its assay procedures with a flame photometer. This assay requies a dilution of 1:200 and numerous errors can occur in this dilution series, as well as in readings on the instrumentation. In seeking a desired small coefficient of variation on the order of 0.1 to 0.5 percent for resolving power, this chemical approach is completely unfeasible for use in evaluating homogeneity of control serum, as adequate resolving power is not present in the method to be used statistically.

Physical methods also have been tried in an attempt to measure homogeneity of control serum, including use of an instrument to measure density of solutions to six significant places. The instrument must be held to within 0.01°C., while making the measurements with a constant temperature thermostated system, and each measurement takes approximately 15 minutes to make. Because of the length of time required to make density measurements, and the fact that in a control group there may be as many as 1000 vials at a time to measure, this procedure is unfeasible in production work for measurement of homogeneity of control serum. Moreover, the value obtained for the density of water must be subtracted from the total density value in order to obtain the density of the solids contained in the solution measured. When the values were subtracted for water, the density values obtained were slightly above the numbers for sodium. The sodium values obtained were approximately 150, or three figures in a very low range. In the density measurements, the values obtained after subtracting the density of water from the density of the control serum were in the range of 300. The resolving power of this density measurement system thus was not sufficient, since multiple measurements of the same serum did not yield coefficients of variation less than 1%.

A method employing the refractive index of the solutions has also been used to measure homogeneity of control serum, but this too has been found unsatisfactory, even with the use of a five-place refractometer. The problem with this method is that it requires subtraction of the density value for water in order to obtain the refractive index of the solids contained in the control serum. This system is not sufficiently reliable statistically to give a low coefficient of variation. The values obtained after the values of water were subtracted from the values obtained for the control serum yielded density values in the 500 to 600 value range, which is insufficient significant figures for the accuracy required. The system required precision temperature control within 0.01°C. and each value took about 5 minutes to measure which was totally unfeasible for production work.

SUMMARY OF THE INVENTION

It has now been discovered that homogeneity of clinical control materials can be determined by adding a radioactive tracer into the bulk control serum tank and mixing with other components so that the radioactive tracer simulates one of the components that is being incorporated in the control serum. The containers filled with the control serum are then analyzed for radioactivity to determine homogeneity of the contents.

Since it is necessary to run quantitative analyses for the various chemical components present in control serum, a selected tracer component must be used, as it can affect some of the biochemical results being tested in the control. Additionally, if a very hot radioactive material with a long half-life is added to the control serum, the control serum can not be used as a control for certain radioactive experiments because the radioactivity present in the serum itself interferes with the reactions to be counted.

Radioactive $^{131}$Iodine has been found to be an ideal radioisotope to use to determine homogeneity of control serum because of its half-life of 8.07 days, as the radioactivity present in the control serum does not affect the value of the control serum approximately one month after addition of $^{131}$I when radioactive measurements are made on it for certain biochemical constituents of the thyroid. For this reason, certain other radioisotopes can not be used in the control serum, for example, $^{125}$I, which has a half-life of 56 days. Since the usual half-life measurements are rated over five half-lives, there would be approximately 10 months' worth of radioactivity in the control serum with the use of $^{125}$I. Radioactive $^{59}$Iron has been ruled out because of the excessive longevity of its half-life of 45.3 days, even though with strict control of the amount of iron added to the control serum the added iron would not interfere with the biochemical quantitation of serum iron or total iron-binding capacity. Radioactive $^{197}$Mercury, which has a half-life of 65 hours, has an insufficiently long total radioactivity, about 300 hours, in which to take all the measurements, including any repeat measurements, and make the necessary mathematical calculations of the decay rate. The decay rate in this case is so rapid that, inasmuch as the counting of each bottle takes place for the two or three minutes required to obtain sufficient radioactivity counts to reduce the error of counting, substantial corrections would have to be made for the change in radioactivity in the control serum.

It has now been discovered that the homogeneity of control serum can be accurately measured by adding about one millicurie of $^{131}$I to 1000 liters of control serum, or about one microcurie of $^{131}$I per liter of control serum. The tracer is mixed in as one of the constituents of the control serum. This level of added iodine is well below any level of iodine which causes any problems in control serum in carrying out experimentations with protein-bound iodine and butanol extractable iodine. It is well-known that excessive amounts of iodine in the control serum yield poor results for assays on certain biochemical constituents deemed important for endocrine functions of the thyroid. The amount of radiation added to the control serum according to the present invention has a theoretical initial count of approximately 2200 disintegrations per minute per ml. of serum, assuming 100% efficiency. The half-life of radioactive $^{131}$Iodine is 8.07 days, and therefore, after 26 days, less than 10 percent of this activity remains in solution.

The radioactive $^{131}$Iodine is added to the control serum and mixed therein in the same manner as any of the other constituents, such as by stirring, as the bottles are filled in a normal filling line. After the bottles have been given their computer analysis for fill variation, they are subjected to a radioactivity count to measure the amount of radioactivity in the fill as a result of the dispersion of the radioactive $^{131}$Iodine throughout the fill. By counting milliliters of solution for several minutes, a statistical analysis procedure is provided which embraces mathematics in the low 0.1 percent coefficient of variation. It is thereby practical to accurately determine the homogeneity of fills for control serum in conformity with the standards proposed by the National Committee for Clinical Laboratory Standards.

Other radioactive tracers, including radioisotopes and radio-labeled compounds, having half-lives ranging from about 4 days to about 15 days also can be used in the practice of this invention.

DESCRIPTION OF THE PREFERRED EMBODIMENTS

EXAMPLE 1

The homogeneity of a control serum is determined as follows: one millicurie of $^{131}$I radiation is added to 1000 liters of control serum to obtain a radiation count of 2200 disintegrations/min/ml of serum. This is well-mixed into the serum by stirring. Samples of the control serum which are used to check for weight variation are tested by withdrawing 1 ml. to 10 ml. aliquots into standard containers and checking the samples in a scintillation counter set up automatically to produce a tape readout.

This example is based on the calculation that one microcurie of radiation is equal to about $22 \times 10^5$ disintegrations/min. By adding 1 microcurie of $^{131}$I radiation to one liter of control serum, approximately 2200 disintegrations/min/ml of serum are obtained. The half-life of $^{131}$Iodine is 8.07 days, with both beta and gamma emission. Therefore, after 26 days, less than 10 percent of the activity of the $^{131}$I remains in the control serum.

EXAMPLE 2

A production line of control serum is set up to provide a fill rate of 150 vials per minute in the 5 ml. fill, or 100 vials per minute in the 10 ml. fill, or 50 vials per minute in the 50 ml. fill, from a 1000 liter batch of control serum dispensed through 6 or 8 heads. Thus, employing the 10 ml. fill size, 100,000 vials are filled in about 1000 minutes. Homogeneity of the control serum is determined by employing the radioactive tracer method as in Example 1 and the inter-vial differences in concentration are found to be equivalent to a coefficient of variation less than 0.5%, employing a 1–2% statistical sample.

It will be understood that the specific examples of the present invention set forth above are given by way of illustration and not limitation and that many modifications and variations of the compositions of this invention can be made without departing from the spirit and scope of the invention. Accordingly, this application for Letters Patent is intended to cover all such modifications and variations as would reasonably fall within the scope of the appended claims.

What is claimed is:

1. A method of determining homogeneity of clinical control serum comprising adding batchwise to the bulk control serum a radioactive tracer having a halflife of from about 4 days to about 15 days, filling standard containers with the control serum containing the radioactive tracer, analyzing said filled standard containers in a radiation counter to determine the amount of radioactivity present in said containers and comparing the inter-container differences in said radioactivity.

2. The method of claim 1 wherein the radioactive tracer is $^{131}$Iodine.

3. The method of claim 2 wherein one microcurie of $^{131}$I is added per liter of control serum.

* * * * *